(12) United States Patent
Samson

(10) Patent No.: US 6,185,442 B1
(45) Date of Patent: *Feb. 6, 2001

(54) VALVE CONTROLLED FLOW INTO A TUBE

(76) Inventor: Ilan Zadik Samson, 8a Chesterford Gardens, London NW3 7DE (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/973,696

(22) PCT Filed: Jun. 7, 1995

(86) PCT No.: PCT/GB96/01359

§ 371 Date: Dec. 8, 1997

§ 102(e) Date: Dec. 8, 1997

(87) PCT Pub. No.: WO96/41570

PCT Pub. Date: Dec. 27, 1996

(30) Foreign Application Priority Data

Jun. 8, 1995 (GB) .................................. 9511660

(51) Int. Cl.[7] ............................................. A61B 5/04
(52) U.S. Cl. ......................... 600/376; 600/387; 607/149
(58) Field of Search ................................. 600/373, 376, 600/382, 383, 386, 387, 338; 607/149; 604/35

(56) References Cited

U.S. PATENT DOCUMENTS 4,537,197 * 8/1985 Hulka .
4,938,218 * 7/1990 Goodman et al. .
5,345,935 * 9/1994 Hiesh et al. .
5,833,622 * 11/1998 Meathrel et al. ................... 600/511

FOREIGN PATENT DOCUMENTS 1535432   7/1968  (FR) .
 392847   5/1933  (GB) .

* cited by examiner

Primary Examiner—Linda C. M. Dvorak
Assistant Examiner—Roy Gibson
(74) Attorney, Agent, or Firm—Richard M. Goldberg

(57) ABSTRACT

Vacuum in a non-invasive medical probe having a source of vacuum interconnected with a suction cup by a resilient walled tube, is reduced in a controlled manner by creating a valve aperture in the wall of the tube at a desired location through which aperture no appreciable leakage will occur when vacuum is applied and the tube is in a relaxed state, whereby with the suction cup secured by vacuum on a patient's skin, application of a force to the tube wall will open the aperture and permit a controlled reduction of vacuum in the suction cup to a specified amount. Releasing the force permits the aperture to close so that lower vacuum is maintained and the suction cup continues to be secured on the patient's skin. In a preferred application there is provided a probe adapted for application to the scalp of a fetus with the rim of the suction cup in sealing contact with the surface of the scalp. There is also provided a method of enabling a controlled flow into a resilient walled tube inside which the pressure is lower than outside the tube, by creating a valve aperture in the wall of the tube in a desired location through which no appreciable leakage will occur when the tube is in a relaxed state. The aperture opens on application of a force to the tube wall and permits a controlled flow therethrough into the tube, and the aperture closes when the force is released.

26 Claims, 5 Drawing Sheets

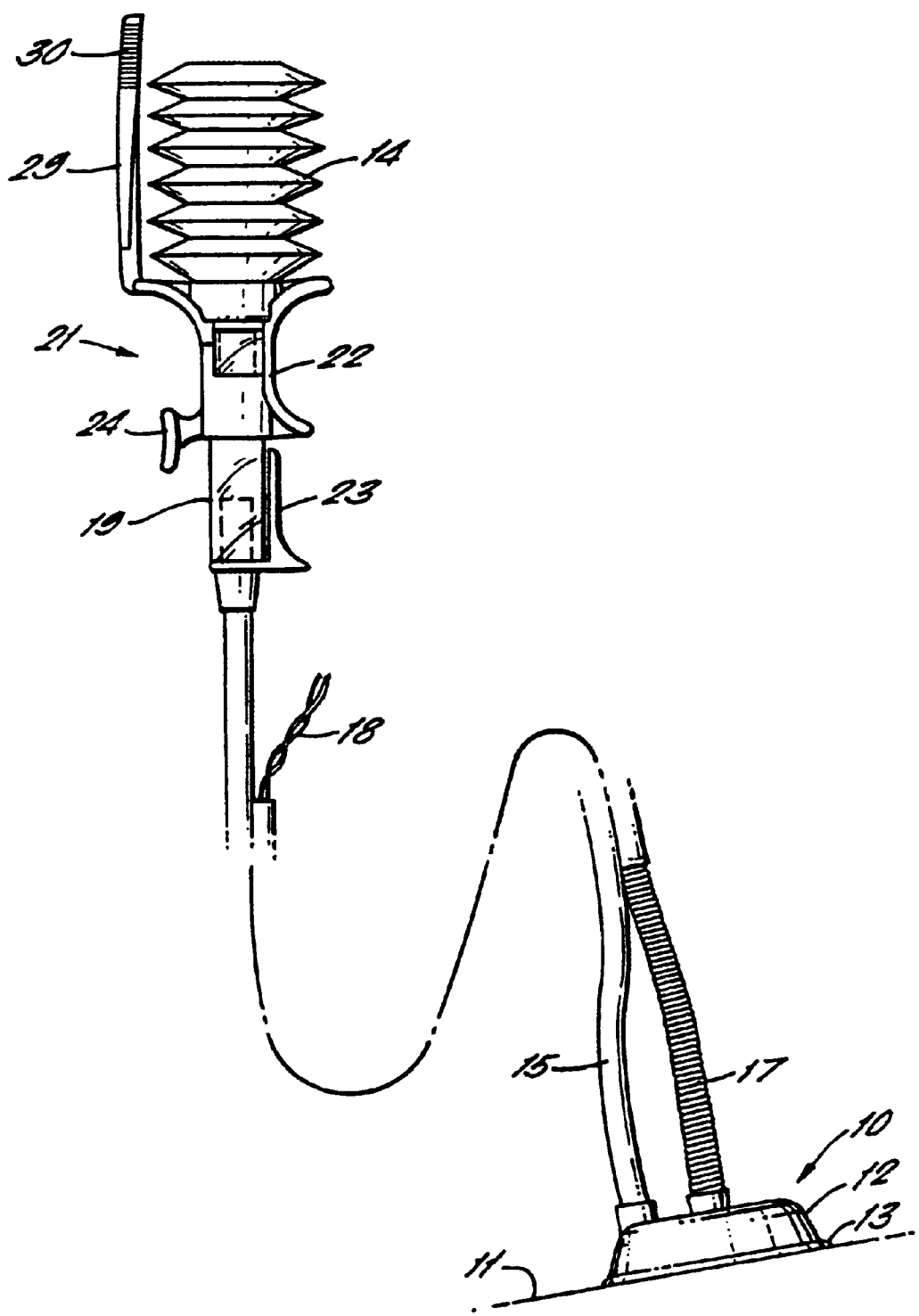

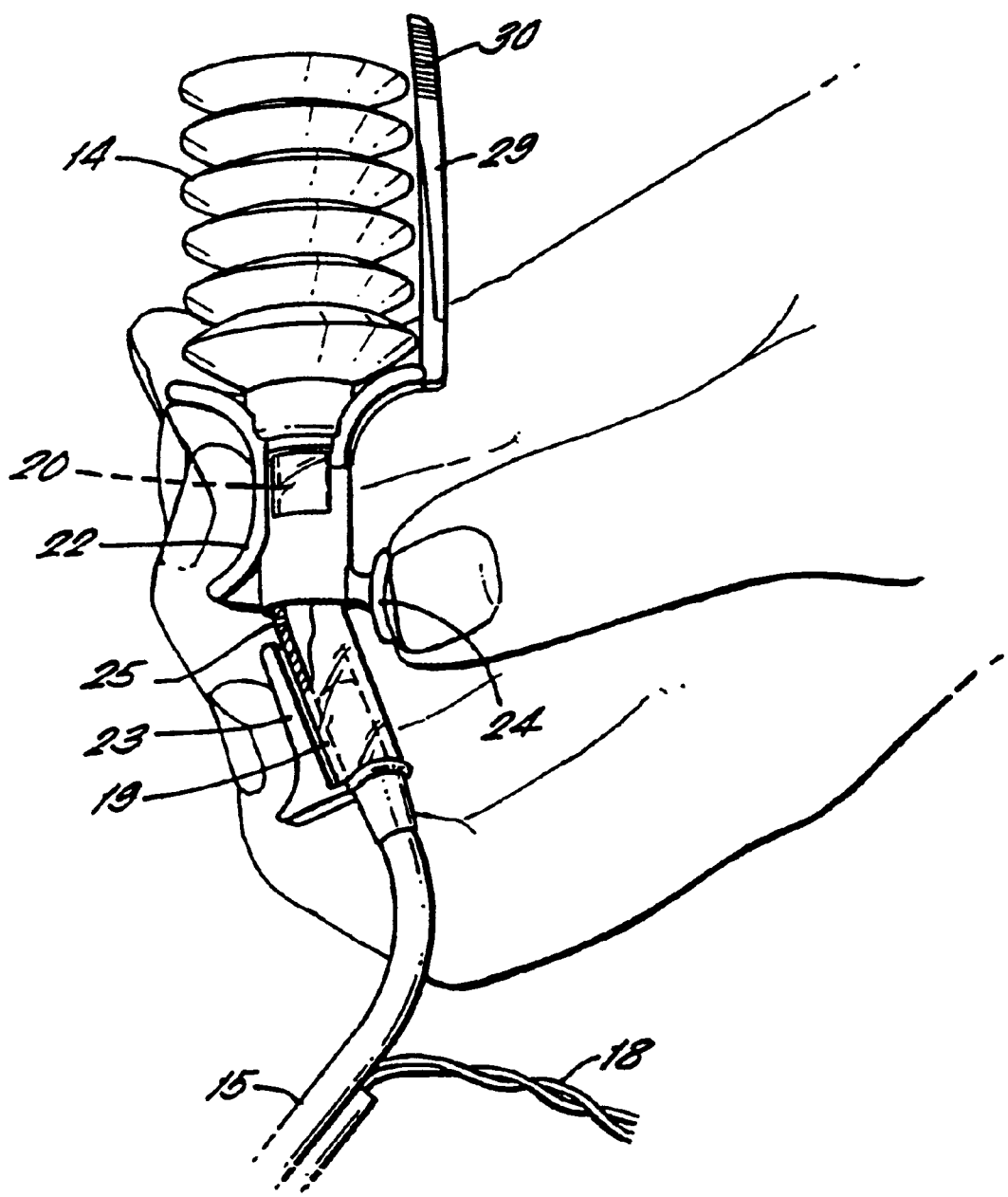

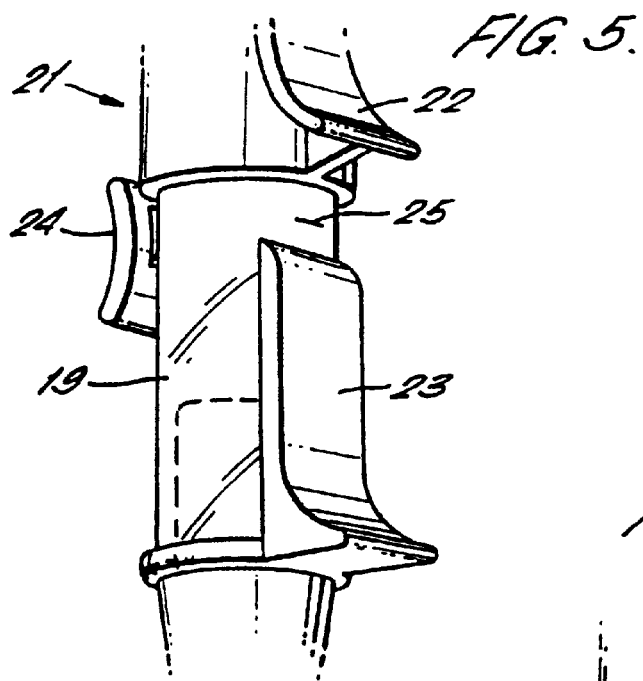
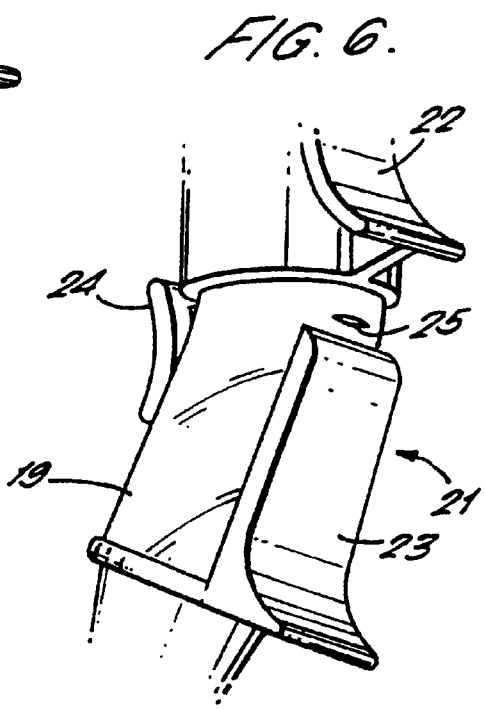
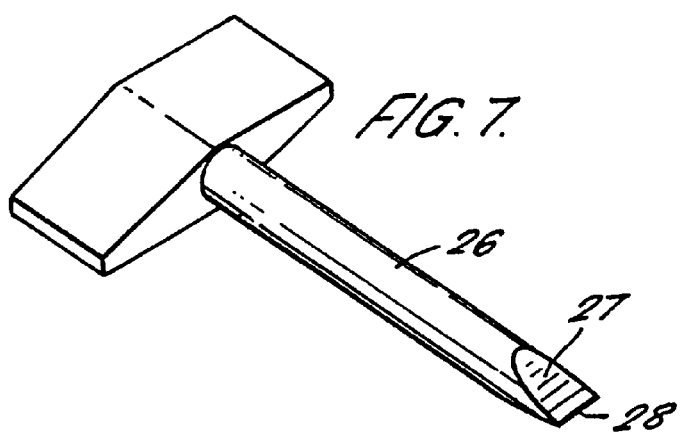

VALVE CONTROLLED FLOW INTO A TUBE

This invention relates to a method and apparatus for the valve controlled flow into a tube inside which the pressure is lower than outside the tube. More particularly, but not exclusively, the invention involves the control of pressure/vacuum internally or externally of the tube, for example, the controlled reduction of vacuum in the tube. In one specific arrangement, the invention relates to a non-invasive medical probe in which a suction cup is secured to a patient's skin, for example the scalp of a fetus, and a method of using the probe.

In EP-A-0525021 there is described a non-invasive medical probe for monitoring a patient's condition. The probe comprises a source of suction, which may be a bellows, or other type of pump, connected by a tube to a resilient walled suction cup for application to a patient's skin. With the suction cup in contact with the patient's skin, the bellows or other pump is actuated to apply vacuum through the tube to secure the cup to the patient's skin. Mounted within the cup is an electrode for making contact with the patient's skin following evacuation of the cup, the resilience and form of the cup being such that the resilient wall deforms so that the electrode is drawn down relative to the peripheral rim of the cup and makes the required contact with the patient's skin. A signal is thereby obtained at the skin surface which is responsive to a varying condition of the patient. In the particular embodiment described, the suction cup is for attachment to the scalp of a fetus with the rim of the cup in sealing contact with the surface of the scalp.

A relatively high vacuum is required to secure the suction cup. The probe needs to remain attached for long durations, e.g. hours, but this creates a red mark on the skin the size of the suction cup. While not harmful, the mark is unsightly and may take up to a day to fade away. It is thus undesirable.

However, it has been found that the level of vacuum which is necessary to maintain the cup in place even during movements of the fetus head can be substantially lower than the initial vacuum necessary to secure the cup.

According to the invention there is provided a method of controllably reducing vacuum in a noninvasive medical probe having a source of vacuum interconnected with a suction cup by a resilient walled tube, comprising creating a valve aperture in the wall of the tube at a desired location through which aperture no appreciable leakage will occur when vacuum is applied and the tube is in a relaxed state, whereby with the suction cup secured by vacuum on a patient's skin, application of a force to the tube wall will open the aperture and permit a controlled reduction of vacuum in the suction cup to a specified amount, and releasing the force will permit the aperture to close so that lower vacuum is maintained and the suction cup continues to be secured on the patient's skin.

The step of maintaining lower vacuum mentioned throughout includes either constant or varying vacuum consistent with the suction cup or other applicator remaining secured.

In the preferred embodiment of the invention the probe is adapted for application to the scalp of a fetus with the rim of the suction cup in sealing contact with the surface of the scalp.

The invention also provides a method of enabling a controlled flow into a resilient walled tube inside which the pressure is lower than outside the tube, comprising creating a valve aperture in the wall of the tube in a desired location through which no appreciable leakage will occur when the tube is in a relaxed state, but which aperture will open on application of a force to the tube wall and permit a controlled flow therethrough into the tube, and which aperture will close when the force is released.

The invention further provides a method of controlling flow into a resilient walled tube inside which the pressure is lower than outside the tube, which tube has in its wall a preformed valve aperture capable of opening and closing when a force on the tube is respectively applied and released, the method comprising applying said force to open the aperture and to permit a controlled flow therethrough into the tube, and releasing said force so that the aperture closes and the flow stops.

The term controlled flow means flow which can be accurately interrupted at predetermined levels of pressure inside or outside the tube and/or the magnitude of the flow can be accurately adjusted. Such interruption is effected by releasing said force to allow the aperture to close, and adjusting the flow is effected by varying the applied force.

In one embodiment, the tube contains a vacuum, and upon opening the valve aperture the vacuum in the tube is controllably reduced so that lower vacuum is maintained in the tube. Preferably the tube interconnects a source of vacuum and a suction applicator.

Alternatively, upon opening the valve aperture, an overpressure outside the tube is controllably reduced or a controlled flow into the tube is generated. Preferably the portion of the tube containing the valve aperture is located or adapted for location in a chamber containing a fluid at said higher pressure. In this case, the force to open the valve aperture may be remote controlled from outside the chamber.

Preferably the vacuum reduction/pressure flow occurs at a substantially constant rate and/or amount.

It is also preferred that said force on the tube wall is applied by bending. Preferably the bending force acts through the valve aperture thereby opening the valve aperture.

The valve aperture may be created by piercing the tube wall radially, e.g. by a needle having an end which is chamfered to a V-shape to form a line end. Preferably the line end of the needle is orientated transversely to the axis of the tube.

Slicing transversely through a resilient tube to a depth which reaches the inside is known for creating a valve which opens when the tube is bent and shuts when the tube returns to a relaxed state, but the ingress of air during bending of the tube cannot be controllably stopped at a specific level or the rate of flow adjusted, especially when a relatively small quantity of fluid is involved.

The invention still further provides a noninvasive medical probe comprising a non-invasive medical probe comprising a source of vacuum interconnected with a suction cup by a resilient walled tube, the cup being adapted to be secured by vacuum on a patient's skin, wherein means are provided for controllably reducing the vacuum to a specified amount, after which lower vacuum can be maintained until the cup is removed.

Preferably the control means are provided in a tube and preferably is a valve aperture in the wall of the tube at a desired location through which aperture no appreciable leakage will occur when vacuum is applied and the tube is in a relaxed state, whilst with the suction cup secured on the patient's skin application of a force to the tube wall will open the aperture and permit a controlled reduction of vacuum in the suction cup to the specified amount, and releasing the force will permit the aperture to close so that lower vacuum is maintained and the suction cup continues to be secured on the patient's skin.

The source of suction is preferably a bellows attached to one end of the tube.

For bending the tube in a specific manner and location to open the valve aperture, the tube is preferably provided with finger holding means, preferably adapted to be used single-handedly.

Means may be provided for measuring the reduction in vacuum. The measuring means may be a calibrated elongate member, which in the case of the source of suction being a bellows or other expandable means for creating suction extends longitudinally of the suction means.

By way of example, a specific embodiment in accordance with the invention will be described with reference to the accompanying drawings in which:

FIG. 3 shows the suction cup secured to the head of a fetus and the bellows partially expanded;

FIG. 4 shows the tube portion bent and the vacuum reduced to a specified amount, the bellows still being partially contracted;

FIG. 5 is a detail of the tube portion in the vicinity of the slit aperture provided for controllably reducing the vacuum;

FIG. 6 is a similar view to FIG. 5, showing the tube portion bent and the slit aperture open; and FIG. 7 illustrates a needle for creating the slit aperture in the tube portion.

Figure 1:
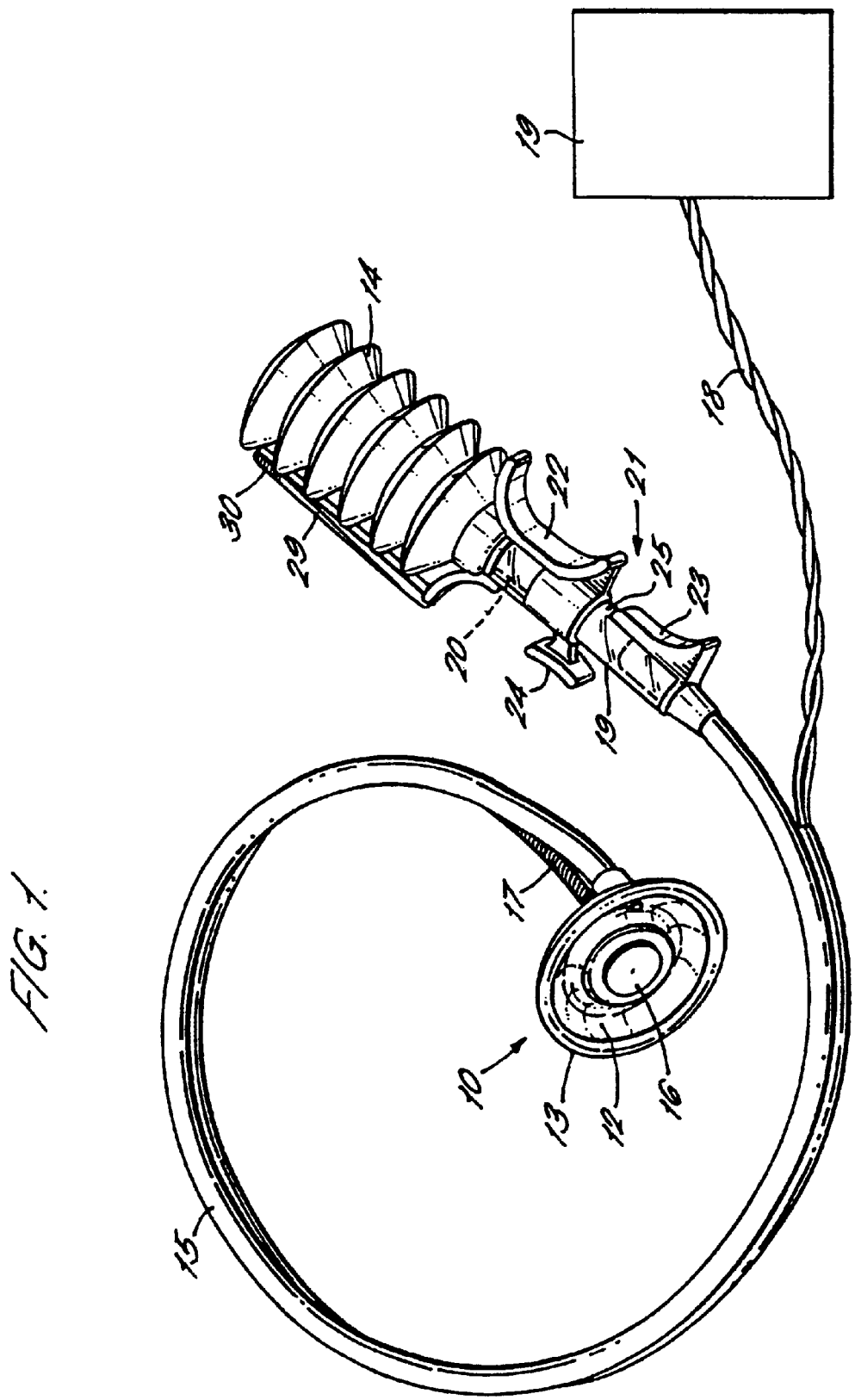
FIG. 1 is a perspective view of a non-invasive medical probe having a bellows interconnected to a suction cup by a resilient walled tube.

This example concerns a non-invasive probe of the same general type as the probe described in EP-A-0525021.

Referring to the drawings, the probe has a suction cup 10 intended for attachment to the head 11 of a fetus for the purpose of monitoring characteristics of the fetus. However, the suction cup is also capable of being applied to a patient's skin more generally, and the invention is not limited to the application of the suction cup on a fetus.

The suction cup 10 has a resilient wall 12 and a peripheral rim 13 whereby vacuum from a vacuum source secures the cup in the desired location. In this embodiment, the vacuum source is a bellows 14 interconnected to the suction cup by a tube 15.

Mounted within the suction cup is an electrode 16 for making electrical contact with the fetal skin. A second electrode formed of coiled wire 17 is provided outside the suction cup for making contact with the vaginal wall. Both electrodes are connected by wiring 18 to diagnostic monitoring apparatus 19.

Figure 2:
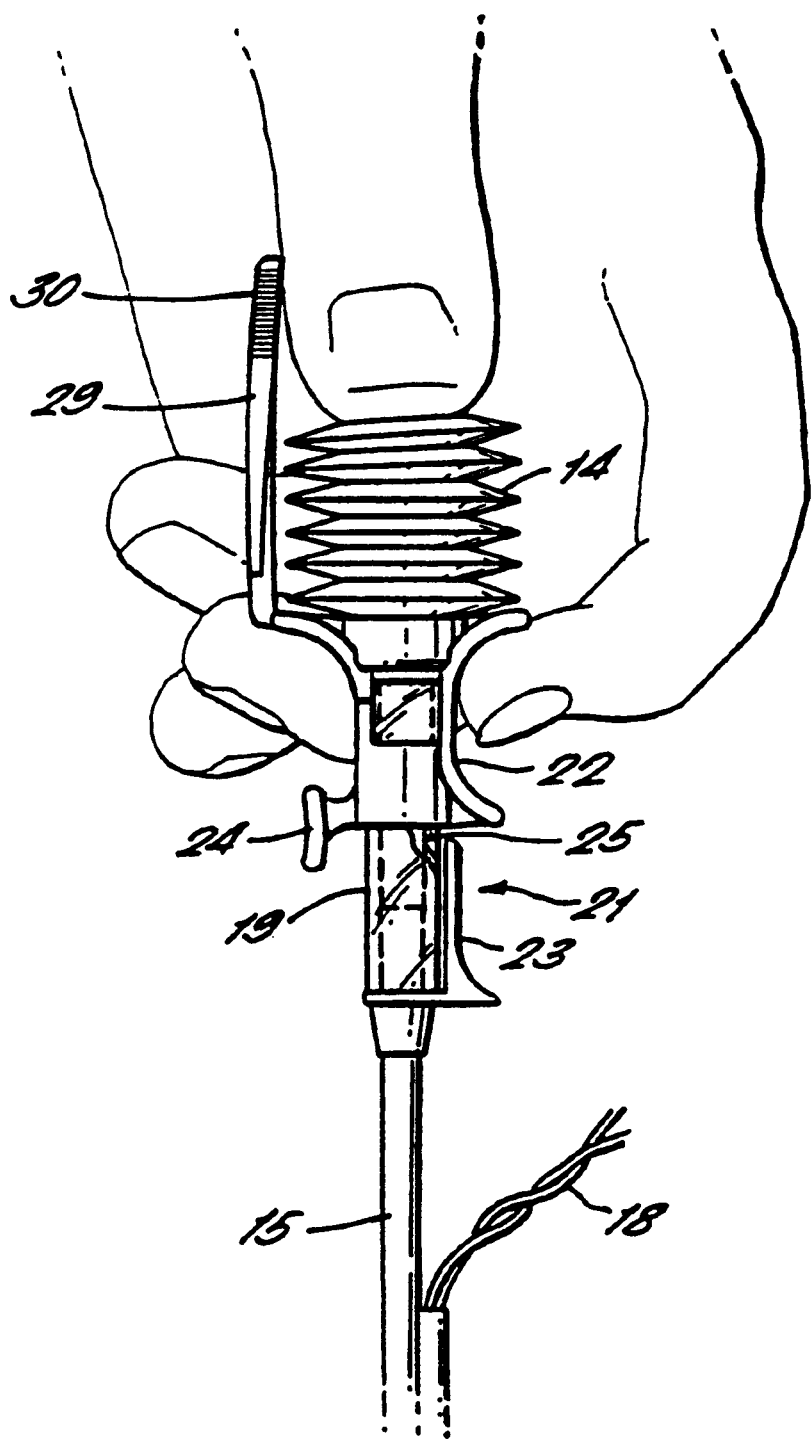
FIG. 2 illustrates the bellows fully compressed prior to securing the suction cup on a patient's skin and the tube portion adjacent to the bellows in a relaxed state.

Therefore, as described in EP-A-0525021, the probe is used by holding the suction cup 10 in contact with the head 11 of a fetus with one hand, whilst preferably holding the bellows 14 fully contracted (FIG. 2) with the other hand. Allowing the bellows to expand will apply vacuum within the suction cup 10 which causes the resilient wall of the cup to deform by bending and to draw down the electrode 16 into contact with the scalp of the fetus as the cup becomes secured on the fetal head (FIG. 3).

At this stage, the bellows 14 is still partly contracted because a relatively high vacuum, typically between 300 and 500 millibars, has been applied to secure the probe in position. It is often required that the probe is kept secured for some time, perhaps a few hours, and such a level of vacuum can create a temporary marking of the fetal skin which is undesirable. However, it has been found that a lower vacuum of, say, 40 to 100 millibars is sufficient to retain the cup 10 in place despite movements of the head of the fetus.

For the purpose of reducing the level of vacuum to a specified amount, there are provided tubular valve control means which will now be described in detail.

The valve means comprises a short intermediate tube portion 19 between the tube 15 and the bellows 14. The intermediate tube portion 19 is impermeably sealed to a funnel 20 of the bellows at one end, and to the adjacent end of the tube 15 at the other end. In this embodiment, the internal diameter of the tube portion 19 is greater than the diameter of the tube 15 and is thus constructed separately from the tube 15. Mounted on the tube portion 19 is a finger holding means 21 adapted to be held between two fingers and thumb of the user's hand which has previously actuated the bellows to apply the vacuum. In this embodiment, the finger holding means are two individual parts mounted at either end of the tube portion 19.

Between the finger recesses 22, 23 on one side of the tube portion 19, and therefore on the opposite side from the thumb pusher 24, there is created a transversely orientated narrow slit aperture 25 which extends radially through the tube wall. In this embodiment the slit 25 is formed by a needle 26 having an end 27 chamfered by grinding on opposite sides to a V-shape (FIG. 7). The end 27 is thereby pointed with a line edge 28, and for creating the slit 25 the needle is orientated with the line edge transversely to the axis of the tube portion 19. It has been found that use of such a needle in this manner creates an aperture 25 which will not leak, at least to an appreciable extent, when vacuum is applied and the tube portion 19 is in a relaxed state (FIG. 5). However, when inward finger/thumb pressure is applied, the tube portion 19 will bend and the slit 25 opens (FIG. 6). Vacuum within the tube portion 19 is thereby reduced, and the bellows 14 will expand by a corresponding amount.

Attached to the part of the finger holding means 21 adjacent the bellows 14 is a calibration stick 29 extending parallel to the bellows. At the free end of the stick 29, markings 30 are provided which are calibrated to show the user the extent by which the bellows 14 has expanded and thus the extent by which the vacuum has reduced.

Alternatively, other measuring means may be provided which essentially comprises a non-expanding elongate member which remains stationary relative to a part of the bellows or other expandable means for creating suction, such as a syringe, whereby it is capable of measuring expansion of the bellows or other suction means.

In use, the vacuum tends to constrict the valve slit 25. Hence as the vacuum becomes less, the slit will open further for a given degree of bending of the tube portion 19. This compensates for the reduced draw of the reduced vacuum, and thus results in a flow rate and a vacuum reducing rate which are substantially constant. The rate of flow and thus the rate of vacuum reduction can be controlled by varying the amount of bending.

When the vacuum has been reduced to a specified amount, the thumb pressure is removed, and the tube portion 19 returns to its relaxed state whereby the slit recloses. The lower vacuum, which is sufficient to retain the cup 10 secure on the fetus head, is maintained until the probe is removed by dislodging the cup either by further bending of the tube portion 19 to reopen the valve means or by depressing the bellows 14. Indeed at any time whilst the probe is still secured, a further reduction of vacuum could be achieved, if desired, by repeating the cycle of bending and releasing the tube portion 19 so that the slit opens and closes again.

The resilient material of which the tube portion 19 is formed is suitable for piercing to achieve the slit aperture 25 which is capable of opening and closing immediately so that when the slit is closed the level of applied vacuum is maintained in the cup 10. The material is also chosen so that it will not cross-link, i.e. it will not naturally reseal itself. Furthermore, for the medical application described above, a material is selected which is inert to gamma irradiation by which the probe as a whole is sterilised before being packaged, and in the case of use in the U.S.A. the material requires to be a material approved by the Federal Drugs Administration (FDA).

It will be appreciated that the suction probe described above is a disposable item. The vacuum control means thus has to be inexpensive, and in the embodiment described the bellows 14 advantageously acts as a gauge to determine the amount by which the vacuum has been reduced, the expansion of the bellows being measured against the calibrated stick 29.

The tube portion 19 preferably has a wall thickness so that it will not buckle when it is bent by the finger/thumb pressure. Also, the fact that the tube portion 19 is relatively short and is held rigidly on either side of the slit aperture 25, enhances the ability of the slit to open when the free, central part of the tube portion is bent, and to reclose when the tube portion straightens after the finger/thumb pressure has been removed. The slit aperture 25 is thus self-closing.

An important advantage of the embodiment described above is that the valve aperture 25 allows the total flow of air which would be required to reduce the vacuum from the applied vacuum to zero, to be only a few cc, for example as low as 1 cc.

The invention is not restricted to the specific details of the embodiment described above. For example, the probe may be used in other applications besides monitoring the characteristics of a fetus.

Also, the principle of reducing vacuum in a tube to a specified amount in a controlled manner may be employed in other applications in which a source of vacuum is interconnected to a suction applicator by a tube. The term suction applicator includes any environment, e.g. a chamber, in which suction is to be applied. The tube may readily be provided with a resilient walled portion having a valve aperture of a kind which is capable of opening and resealing in the manner described, and preferably has finger holding means for applying the necessary pressure to open the aperture and thereby reduce the vacuum in the tube and the suction applicator. Alternatively, other means may be provided for opening the aperture, which means may be remotely actuated.

Furthermore, instead of the valve aperture being employed to reduce vacuum in the tube, the same principle can be applied to other situations in which the pressure inside the tube is lower than the pressure outside the tube. In one case, the tube portion containing the valve aperture is located, or adapted for location, in a chamber containing a fluid, e.g. air, at a higher pressure than the pressure in the tube. By bending the tube, the valve aperture can be opened to allow a controlled air flow through the valve aperture into the tube either to lower the pressure in the chamber to a specified amount, or to supply air to the tube from the chamber at a controlled rate and amount. In each case, as explained above, the air flow through the valve aperture will be at a substantially constant rate for a given degree of bending, and can be varied by varying the bending force. On releasing the bending force, the valve aperture will close maintaining lower pressure in the chamber or halting the air flow from the chamber into the tube.

By way of example, the tube may be bent internally of a sealed chamber by a rod inserted within the tube to the vicinity of the valve aperture in the tube wall, or other remote controlled means.

What is claimed is:

1. A method of controlling flow into a resilient walled tube inside which the pressure is lower than outside the tube, which tube has in its wall a preformed valve slit created by piercing the wall of the tube with the end of a tool whereby the slit is capable of opening and self closing under said lower pressure within the tube when a force on the tube is respectively applied and released, the method comprising applying said force to open the slit and to permit a controlled flow therethrough into the tube, and releasing said force so that the slit closes and the flow stops.

2. A method of securing a non-invasive medical probe to a patient's skin, the probe comprising a source of vacuum interconnected with a suction cup by a resilient walled tube structure, the cup being adapted to be secured by vacuum on a patient's skin, comprising the steps of:

applying an initial level of vacuum to said suction cup through said resilient walled tube structure to secure the suction cup by vacuum on the patient's skin, thereafter controllably reducing the vacuum applied to said suction cup to a specified lower amount while the suction cup is secured by vacuum on the patient's skin, and thereafter maintaining said specified lower amount of vacuum while the suction cup is secured by vacuum on the patient's skin, until the suction cup is removed.

3. A method as claimed in claim 2, wherein the reduction of said vacuum is controlled to occur at a substantially constant rate and/or amount.

4. A method as claimed in claim 2, wherein said step of controllably reducing is performed with only one hand.

5. A method as claimed in claim 2, wherein said step of controllably reducing includes the step of controllably reducing the vacuum through the resilient walled tube structure.

6. A method according to claim 2, wherein said initial level of vacuum is in the range of 300–500 millibar applied to attach the suction cup in place.

7. A method according to claim 2, wherein the reduced vacuum is in the range of 40 to 100 millibar.

8. A method as claimed in claim 2, wherein:

the resilient walled tube structure includes a valve slit at a desired location, said slit being self-closing under pressure of the vacuum within the resilient walled tube structure such that no appreciable leakage will occur through the slit when the vacuum is applied and the resilient walled tube structure is in a relaxed state, and the step of controllably reducing the vacuum includes the step of, with the suction cup secured by the vacuum on the patient's skin, applying a force to a tube wall of the resilient walled tube structure to open the slit and permit a controlled reduction of vacuum in the suction cup to the specified lower amount, whereupon release of the force results in the slit closing so that specified lower amount of the vacuum is maintained and the suction cup continues to be secured on the patient's skin.

9. A method as claimed in claim 8, further comprising the step of creating the slit by piercing the wall of the resilient walled tube arrangement with the end of a tool.

10. A method as claimed in claim 9, wherein the step of creating the slit includes the step of inserting a needle having an end chamfered to a line end as the tool into the resilient walled tube structure.

11. A method as claimed in claim 8, wherein the step of controllably reducing includes the step of bending the resilient walled tube structure in the vicinity of the slit to open the slit and thereby reduce the vacuum.

12. A non-invasive medical probe comprising:

a source of vacuum, a suction cup adapted to be secured by vacuum on a patient's skin, a resilient walled tube structure interconnecting the source of vacuum with the suction cup, a vacuum reducing arrangement separate from said source of vacuum and associated with said resilient walled tube structure for reducing the vacuum supplied by said source of vacuum to said suction cup by a specified lower amount in a controllable manner and for maintaining the reduced vacuum to said suction cup until the suction cup is removed.

13. A probe as claimed in claim 12, wherein said vacuum reducing arrangement includes a device to enable a single-handed operation for reducing the vacuum supplied to said suction cup.

14. A probe as claimed in claim 12, wherein the vacuum reducing arrangement is provided in the resilient walled tube structure.

15. A probe as claimed in claim 14, wherein the vacuum reducing arrangement includes a valve slit through a tube wall of the resilient walled tube structure at a desired location, which slit is self closing under pressure of the vacuum within the resilient walled tube structure, such that no appreciable leakage will occur through the slit when the vacuum is applied and the resilient walled tube structure is in a relaxed state, and wherein, with the suction cup secured by vacuum on the patient's skin, application of a force to the wall of the resilient walled tube structure wall will open the slit to provide a controlled reduction of vacuum in the suction cup to the specified lower amount, and releasing the force will result in closing of the slit so that the specified lower amount of the vacuum is maintained and the suction cup continues to be secured on the patient's skin.

16. A probe as claimed in claim 15, wherein the valve slit extends radially through the tube wall and transversely of an axis of the resilient walled tube structure.

17. A probe as claimed in claim 15, wherein the valve slit extends transversely of the resilient walled tube structure such that the force to reduce the vacuum is applied by bending the resilient walled tube structure about an axis of the slit with the slit disposed on the outside of a bend formed in the resilient walled tube structure, thereby opening the slit.

18. A probe as claimed in claim 15, further comprising a finger holding arrangement mounted with the resilient walled tube structure for bending the resilient walled tube structure in a specific manner and location to open the valve slit.

19. A probe as claimed in claim 18, wherein the finger holding arrangement includes a structure that enables the finger holding arrangement to be actuated by only one hand.

20. A probe as claimed in claim 12, wherein the source of vacuum includes a bellows attached to one end of the resilient walled tube structure.

21. A probe as claimed in claim 12, further including a measuring device for measuring the reduction in vacuum.

22. A probe as claimed in claim 21, wherein the measuring device comprises a non-expanding elongate member adapted to measure movement of the source of vacuum as the vacuum is reduced.

23. A probe as claimed in claim 22, wherein the source of vacuum includes an expandable device for creating suction, and the elongate member is fixed relative to a part of the expandable device for measuring expansion of the expandable device.

24. A probe as claimed in claim 22, wherein at least an end of the elongate member is calibrated to indicate the amount of vacuum remaining in the suction cup.

25. A non-invasive medical probe comprising a source of vacuum interconnected with a suction cup by a resilient walled tube structure, the suction cup being adapted to be secured on a patient's skin by a vacuum created within the suction cup by said vacuum source, a vacuum reducing arrangement provided at an end of said resilient walled tube structure remote from the suction cup for controllably reducing the vacuum within the suction cup from a first upper value to a predetermined lower value in relation to said upper value, said vacuum reducing arrangement permitting maintenance of the vacuum at said lower value until the suction cup is to be removed, said source of vacuum comprising a bellows which is expansible to create said vacuum in the suction cup, and further comprising an indicator to indicate a state of contraction of the bellows corresponding to said predetermined lower vacuum value.

26. A non-invasive medical probe comprising a source of vacuum interconnected with a suction cup by a resilient walled tube structure, the suction cup being adapted to be secured on a patient's skin by a vacuum created within the suction cup by said vacuum source, a vacuum reducing arrangement provided at an end of said resilient walled tube structure remote from the suction cup for controllably reducing the vacuum within the suction cup from a first upper value to a predetermined lower value in relation to said upper value, said vacuum reducing arrangement permitting maintenance of the vacuum at said lower value until the suction cup is to be removed, the vacuum reducing arrangement includes a valve aperture in a tube wall of the resilient walled tube structure permitting no appreciable leakage into the vacuum when the tube is in a relaxed state, the aperture being openable by application of a force to the tube wall to permit said reduction of vacuum in the suction cup.

* * * * *